United States Patent
Bayon et al.

(10) Patent No.: US 9,107,978 B2
(45) Date of Patent: Aug. 18, 2015

(54) TEMPLATE FOR BACTERIAL CELLULOSE IMPLANT PROCESSED WITHIN BIOREACTOR

(75) Inventors: Yves Bayon, Lyons (FR); Sébastien Ladet, Lyons (FR); Olivier Lefranc, Chatillon sur Chalaronne (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 374 days.

(21) Appl. No.: 13/125,607

(22) PCT Filed: Nov. 6, 2009

(86) PCT No.: PCT/IB2009/007661
§ 371 (c)(1),
(2), (4) Date: Jul. 11, 2011

(87) PCT Pub. No.: WO2010/052583
PCT Pub. Date: May 14, 2010

(65) Prior Publication Data
US 2011/0262706 A1    Oct. 27, 2011

Related U.S. Application Data

(60) Provisional application No. 61/112,298, filed on Nov. 7, 2008.

(51) Int. Cl.
| | | |
|---|---|---|
| A61F 13/00 | (2006.01) | |
| A61L 27/20 | (2006.01) | |
| A61L 27/56 | (2006.01) | |
| A61L 27/58 | (2006.01) | |
| A61K 9/70 | (2006.01) | |

(52) U.S. Cl.
CPC ........... *A61L 27/20* (2013.01); *A61F 13/00012* (2013.01); *A61L 27/56* (2013.01); *A61L 27/58* (2013.01); *A61F 13/00021* (2013.01); *A61F 13/00059* (2013.01); *A61F 2013/00153* (2013.01); *A61F 2013/00255* (2013.01); *A61F 2013/00314* (2013.01); *A61K 9/70* (2013.01); *Y10T 428/24479* (2015.01)

(58) Field of Classification Search
CPC ................ A61K 9/70; A61F 13/00012; A61F 13/00021; A61F 13/00059; A61F 2013/00153; A61F 2013/00255; A61F 2013/00314
See application file for complete search history.

(56) References Cited

U.S. PATENT DOCUMENTS

| | | | | |
|---|---|---|---|---|
| 3,364,200 | A | * | 1/1968 | Moser et al. .................... 536/56 |
| 4,588,400 | A | * | 5/1986 | Ring et al. ..................... 604/304 |
| 6,071,727 | A | * | 6/2000 | Bungay et al. ................ 435/101 |
| 6,777,227 | B2 | * | 8/2004 | Ricci et al. .................. 435/304.1 |
| 2004/0182261 | A1 | * | 9/2004 | Fernfors et al. ............... 101/125 |
| 2005/0228329 | A1 | * | 10/2005 | Boehringer et al. ............ 602/52 |
| 2007/0213522 | A1 | | 9/2007 | Harris et al. |

FOREIGN PATENT DOCUMENTS

| | | |
|---|---|---|
| EP | 0 396 344 A2 | 11/1990 |
| WO | WO 2006/042287 A2 | 4/2006 |

OTHER PUBLICATIONS

International Search Report PCT/IB2009/007661 dated Sep. 15, 2010.
Uraki et al., "Honeycomb-like Architecture Produced by Living Bacteria", vol. 69, No. 1, Mar. 30, 2007, Abstract only.

* cited by examiner

*Primary Examiner* — Ali Soroush

(57) ABSTRACT

The present invention relates to an implant comprising: a sheet of bacterial cellulose having a macro-pattern positioned on at least a portion thereof. The invention also relates to a method for making such an implant.

7 Claims, 1 Drawing Sheet

TEMPLATE FOR BACTERIAL CELLULOSE IMPLANT PROCESSED WITHIN BIOREACTOR

CROSS-REFERENCE TO RELATED APPLICATIONS

Figure 1:
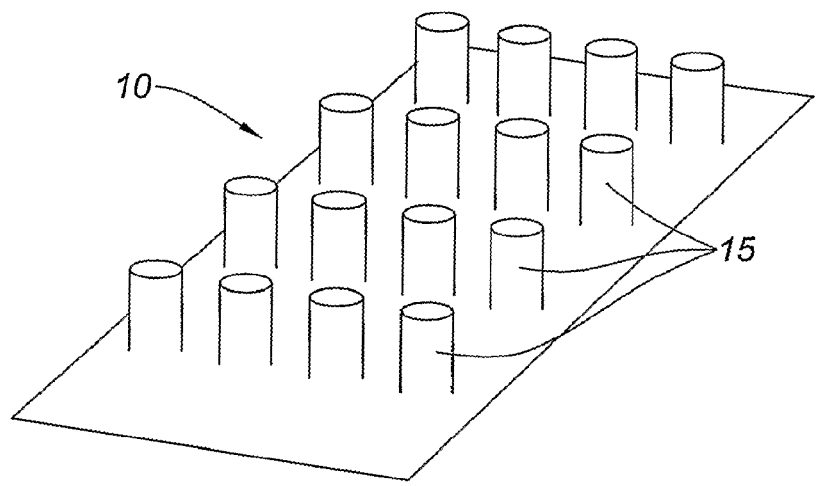

This application is a U.S. National Stage Application filed under 35 U.S.C. §371(a) of International Application No. PCT/IB2009/007661 filed Nov. 6, 2009, which claims the benefit of and priority to U.S. Provisional Application Ser. No. 61/112,298 filed Nov. 7, 2008, the entire contents of which are incorporated by reference herein.

The implants described herein include a sheet of bacterial cellulose having a macro-pattern positioned on at least one side of the sheet.

Methods for producing such implants include culturing bacteria capable of producing a bacterial cellulose in a bioreactor in the presence of a template having a macro-patterned surface.

An aspect of the present invention is an implant comprising:

a sheet of bacterial cellulose having a macro-pattern positioned on at least a portion thereof.

The bacterial cellulose may derived from *Acetobacter xylinum*. The bacterial cellulose may be oxidized.

Another aspect of the present invention is a method of making an implant comprising:

providing a bioreactor having a macro-patterned surface; and culturing a bacteria on the macro-patterned surface, wherein the bacteria is capable of producing a sheet of bacterial cellulose.

The bacteria may be *Acetobacter xylinum*.

Another aspect of the present invention is a method of treating a wound comprising contacting a wound with an implant as described above.

In the present disclosure, the term "implant" is intended to mean a biocompatible or bioresorbable medical device, at least a portion of which can be implanted in the human or animal body.

In the present disclosure, the term "bioresorbable" is intended to mean the characteristic according to which an implant and/or a material is degraded by the biological tissues and the surrounding fluids, in vivo after a given period of time, that may vary, for example, from one day to several months, depending on the chemical nature of the implant and/or of the material.

In the present disclosure, the term "bioreactor" is intended to include any device or system capable of supporting a biologically active environment for growing or culturing materials. In addition to containers or vessels capable of seeding or growing bacteria, the bioreactors may also include the ability to provide agitation, pressure changes, temperature controls, humidity controls, media exchange, and ventilation.

In the present disclosure, the term "sheet" is intended to include generally planar-shaped formats, such as films, foams, pellicles, layers and combinations thereof.

In the present disclosure, the sheet of bacterial cellulose may be produced from bacteria that synthesize cellulose. Cellulose is synthesized by bacteria belonging to the genera *Acetobacter, Rhizobium, Agrobacterium*, and *Sarcina*. Cellulose can be produced by certain bacteria from glucose in the presence of oxygen, (such as, for example, *Acetobacter xylinum*, referenced hereinafter as the "bacteria"), in static conditions or in a bioreactor (see, e.g. U.S. Pat. Nos. 4,912,049 and 5,955,326, the entire disclosures of which are incorporated herein by this reference). Cellulose suitable for use in the present implants can be obtained by the fermentation of the bacteria. In embodiments, a derivative of the cellulose is employed, such as oxidized cellulose resulting from the oxidation of the cellulose by periodic acid or nitrogen dioxide.

Bacterial cellulose possesses inherent characteristics which allow effective promotion of wound healing (see, e.g. U.S. Pat. No. 7,390,492, the entire disclosures of which are incorporated herein by this reference). In this regard, bacterial cellulose displays properties (such as unique multi-layer three dimensional laminar structures) that distinguish it from plant cellulose and other natural polymeric materials. Bacterial cellulose shows excellent wet strength, does not easily breakdown under compression and demonstrates high moisture handling ability.

Figure 2:
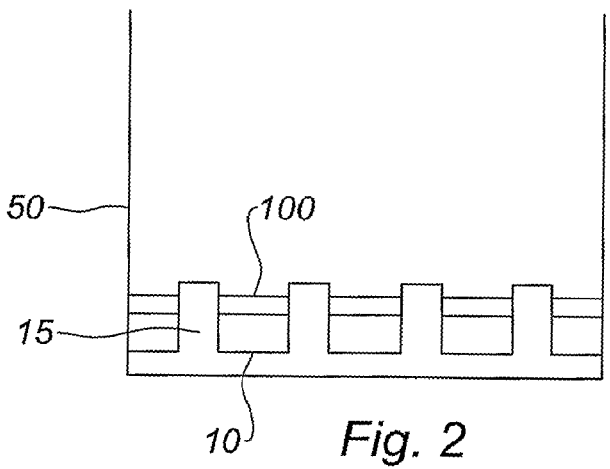

In the present disclosure, at least a portion of the sheet of bacterial cellulose is porous and includes a macro-pattern thereon. The porous sheet 100 is formed on or around a template 10 having a three dimensional ("3D") macro-pattern positioned within the bioreactor 50. (See FIG. 2.) In embodiments, the template is positioned on or near the bottom of the bioreactor. It should be understood that instead of a separate structure positioned within the bioreactor, the template may be formed directly into a surface of the bioreactor, such as, for example, formed into the bottom surface of the bioreactor. The porosity of the cellulose sheet is created during the fermentation process when the cellulose is synthesized by the bacteria in a bioreactor which includes culture media. The cellulose synthesis on and around the template having the 3D macro-pattern formed on at least a portion of the bioreactor can lead to the sheet having a well-defined porosity. Because the sheet is formed in the presence of the template, the macro-pattern is imparted to the sheet during formation without the use of additional processing.

The materials used to form the 3D macro-pattern on a template of the bioreactor are compatible with the culture media, the culture conditions and any other contents in the bioreactor which allows for growth of the bacteria on the predetermined 3D macro-pattern portion of the bioreactor. For example, the template may be made from but not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof, polychloride vinyle (PVC), polycarbonate, polysulfone, fluorocarbones (eg. Teflon® and derivatives, Halar ECTFE [ethylenechlorortrifluoroethylene copolymers)], Tefzel EFTE [ethylene tetrafluorethylene], polyfluoride vinyle [PVDF], stainless steel. The 3D macro-pattern on the template can be designed having any form, geometry or topography which allows for removal of the implant from the bioreactor surface following the biosynthesis of the bacterial cellulose. The materials used to design the 3D macro-pattern, such as peaks, tubes, rods, and spikes, have the ability to withstand the growth of the bacterial cellulose thereby creating a macro-pattern, while retaining a softness and flexibility in order to allow the bacterial cellulose to be withdrawn from the bioreactor without damaging the macro-pattern. For example, as seen in FIG. 1, 3D macro-pattern 10 includes a series of regularly spaced rods 15.

Figure 3:
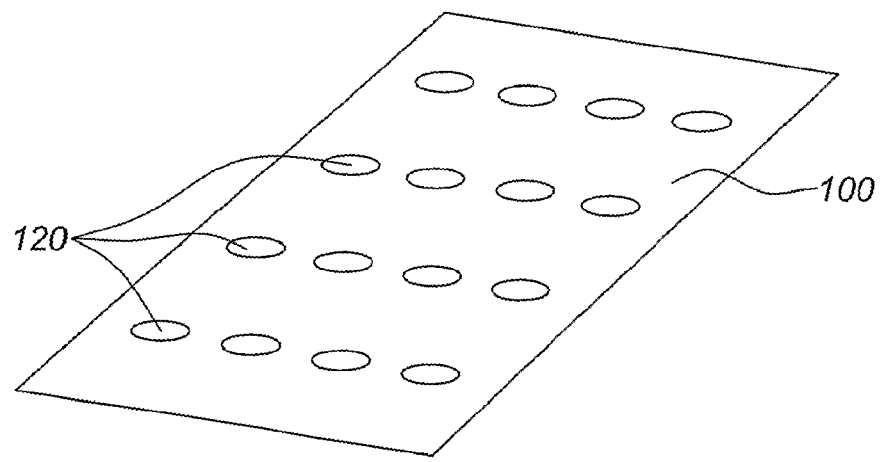

The macro-pattern may create pores, openings or perforations in the sheet having any geometric shape or dimension. For example, the pores may be circular, conical, rectangular, square, oval, elliptical, polygonal and the like. The macro-pattern on the bacterial cellulose sheet improves the implants ability to integrate tissue. As seen in FIG. 3, sheet 100 includes regularly distributed circular openings 120 resulting from culturing bacteria in the presence of the 3D macro-pattern shown in FIG. 1.

The size of the pores may be from about 0.5 mm to 5 mm, in embodiments from about 1 mm to 3 mm.

It should be understood that the macro-pattern needs not pass completely through the sheet (e.g., holes), but rather may be indententions resulting from the sheet being formed around and over at least a portion of the macro-pattern template. In such embodiments, the sheet may have a continuous, not indentented surface for the prevention of post-operative tissular adhesions.

In other embodiments, it should be understood that the macropattern may pass completely through the sheet (e.g., full thickness holes).

The implants described herein are useful for implantation where soft tissues are in need of repair, reinforcement, replacement or augmentation. For instance, the implants may be useful near the abdominal wall, vascular tissue or the pelvic floor. The implants may be easily fixed for surgeries, by any known techniques, among them suturing, stitching, stapling and tacking.

In embodiments, the bacterial cellulose is harvested at the end of the fermentation of the bacteria. The harvested cellulose is subjected to purification and depyrogenation processes. The bacterial cellulose may be oxidized by periodic acid or by nitrogen dioxide before, after, or during the purification and depyrogenation process. In embodiments, the bacterial cellulose may be oxidized when the cellulose is at least partly purified and depyrogenated. The final level of oxidation can be controlled in such a way to produce a resorption time of from several days to several months. The degree of oxidation can be from about 0.1 to about 0.9, in embodiments from about 0.2 to about 0.65.

Other chemical modifications of the bacterial cellulose for the generation of cellulose derivatives are also within the scope of the present disclosure. Cellulose belong to the family of biodegradable, renewable polymers that provides a broad range of important functional properties, and are thus widely used in industry today. However, some of the inherent properties of these polysaccharides limit their utility in certain applications. Therefore, native cellulose are commonly modified by physical, chemical, enzymatic or genetic means in order to obtain specific functional properties (Richardson, et al., Analytica Chimica Acta, 2003; Kennedy, et al., Cellulose and its Derivatives: Chemistry, Biochemistry and Applications, Ellis Horwood, Chichester, 1985; Guilbot, et al., The Polysaccharides, G. Aspinall (Ed.), Academic Press, New York, 1985). Native cellulose has an intrinsic lack of solubility in water and most organic solvent systems which constitutes a major obstacle for utilizing cellulose in many industrial applications. It may be a goal to chemically derivatize the bacterial cellulose in such a way to obtain derivatives soluble in organic solvents, for an easier remodeling of the bacterial cellulose, for example.

The present implants which include a bacterial cellulose sheet having a 3D macro-pattern may advantageously maintain one or more of the original properties of bacterial cellulose sheets (such as, for example, high biocompatibility, extreme hydrophilicity, unique multi-layered three dimensional laminar structures which provide its moisture handling properties, excellent wet strength, high resistance to breakdown under compression, conformability, absence of generation of harmful particles of the cellulose mesh after rubbing against surrounding tissues or erosion at sharp edges of tissues—e.g., sharp edges of bone and cartilage tissues) while inducing controlled porosity directly during the biosynthesis within the sheets for better tissue integration and cell colonization when implanted. Bacterial cellulose sheets can have superior mechanical properties compared to other bioresorbable implants.

Medical implants in accordance with this disclosure may be produced at a predetermined size or produced in large sheets which may be cut to sizes appropriate for the envisaged application. The medical implants may be packaged in single or dual pouches and sterilized using conventional techniques, such as, but not limited to, irradiation with beta (electronic irradiation) or gamma (irradiation using radioactive cobalt) rays at about 25 KGy to about 35 KGy, and/or sterilized by ethylene oxide.

It will be understood that various modifications may be made to the embodiments disclosed herein. Thus, those skilled in the art will envision other modifications within the scope and spirit of the disclosure.

The invention claimed is:

1. A method of making an implant comprising:
providing a bioreactor having a macro-patterned surface formed into a bottom surface of the bioreactor; and
culturing a bacteria on the macro-patterned surface forming a sheet of bacterial cellulose imparted with the macro-pattern without the use of additional processing, wherein the sheet includes pores of a size from about 0.5 mm to 5 mm and the pores do not pass completely through the sheet.

2. The method of making an implant of claim 1 wherein the bacteria is *Acetobacter xylinum*.

3. The method of claim 1 further comprising the step of oxidizing the bacterial cellulose.

4. The method of claim 3 wherein the bacterial cellulose is oxidized with a degree of oxidation from 0.1 to 0.9.

5. The method of making an implant of claim 1 wherein the macro-patterned surface includes a 3-D macro pattern selected from peaks, tubes, rods and spikes.

6. The method of making an implant of claim 1 wherein the macro-patterned surface includes a 3-D macro pattern including a plurality of regularly spaced rods.

7. The method of making an implant of claim 6 wherein the size of the pores is from about 1 mm to 3 mm.

* * * * *